(12) United States Patent
Lebel et al.

(10) Patent No.: US 7,569,030 B2
(45) Date of Patent: Aug. 4, 2009

(54) SAFETY LIMITS FOR CLOSED-LOOP INFUSION PUMP CONTROL

(75) Inventors: Ronald J. Lebel, Sherman Oaks, CA (US); Timothy Starkweather, Simi Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 1079 days.

(21) Appl. No.: 10/979,980

(22) Filed: Nov. 3, 2004

(65) Prior Publication Data

US 2005/0065465 A1 Mar. 24, 2005

Related U.S. Application Data

(62) Division of application No. 10/033,530, filed on Dec. 26, 2001, now Pat. No. 6,827,702.

(60) Provisional application No. 60/318,062, filed on Sep. 7, 2001, provisional application No. 60/335,664, filed on Oct. 23, 2001.

(51) Int. Cl.
*A61M 31/00* (2006.01)

(52) U.S. Cl. ........................................................ 604/65

(58) Field of Classification Search ............. 604/65–67, 604/31, 48, 500–504, 131; 128/DIG. 12, 128/DIG. 13
See application file for complete search history.

(56) References Cited

U.S. PATENT DOCUMENTS

| | | | |
|---|---|---|---|
| 5,139,020 A | 8/1992 | Koestner et al. | |
| 5,536,249 A | 7/1996 | Castellano et al. | |
| 5,558,640 A | 9/1996 | Pfeiler et al. | |
| 5,593,390 A | 1/1997 | Castellano et al. | |
| 5,713,856 A | 2/1998 | Eggers et al. | |
| 5,728,074 A | 3/1998 | Castellano et al. | |
| 5,730,137 A | 3/1998 | Amano et al. | |
| 5,925,021 A | 7/1999 | Castellano et al. | |
| 6,221,009 B1 | 4/2001 | Doi et al. | |
| 6,354,299 B1 | 3/2002 | Fischell et al. | |

(Continued)

FOREIGN PATENT DOCUMENTS

JP 1-317452 12/1989

(Continued)

OTHER PUBLICATIONS

Office Action dated Sep. 9, 2008 issued from related Japanese patent application No. 2003-526454.

(Continued)

*Primary Examiner*—Manuel A Mendez
(74) *Attorney, Agent, or Firm*—Foley & Lardner LLP

(57) ABSTRACT

A system and process for providing safety limits on the delivery of an infusion formulation by an infusion pump system in response to a sensed biological state. The safety limits may comprise user-initiated event signals corresponding to events that may significantly affect the biological state. The safety limits may further comprise user-initiated event ranking signals for respective events which specify a degree, quantity, or measure for the respective event. The user-initiated event and event ranking signals may be communicated to a computing element associated with the infusion pump by an associated communication device having a user interface which comprises a plurality of user-selectable operators for entering information about the events and event rankings.

20 Claims, 9 Drawing Sheets

U.S. PATENT DOCUMENTS 6,453,195 B1 9/2002 Thompson
6,544,212 B2 * 4/2003 Galley et al. .................. 604/31

FOREIGN PATENT DOCUMENTS

| | | |
|---|---|---|
| JP | 7-132142 | 5/1995 |
| JP | 7-148253 | 6/1995 |
| JP | 9504974 | 5/1997 |
| JP | 10-504729 | 5/1998 |
| WO | WO 95/13838 | 5/1995 |
| WO | WO98/02086 | 1/1998 |
| WO | WO 00/10628 | 3/2000 |
| WO | WO 00/74753 A1 | 12/2000 |

OTHER PUBLICATIONS

PCT International Search Report as issued in International Application No. PCT/US02/28022, Mailing date Apr. 23, 2003.

* cited by examiner

SAFETY LIMITS FOR CLOSED-LOOP INFUSION PUMP CONTROL

RELATED APPLICATIONS

This application is a divisional of application Ser. No. 10/033,530 filed Dec. 26, 2001, now U.S. Pat. No. 6,827,702 which is in turn claims the benefit of prior filed U.S. Provisional Application Ser. Nos. 60/318,062 filed Sep. 7, 2001, and 60/335,664 filed Oct. 23, 2001, The entirety of each which are incorporated herein by reference.

BACKGROUND OF THE INVENTION

1. Field of the Invention

The present invention relates generally to infusion pump systems for the delivery of infusion formulations and, in particular, to an implantable infusion pump system and process for delivering insulin to a user based in part on user-initiated signals which correspond to events which may affect the glucose level of the user.

2. Description of Related Art

In the medical arts, implantable infusion pumps are used for the programmed delivery of measured doses of an infusion formulation. (An infusion formulation is defined in the present disclosure as the substance being delivered by the infusion pump. This substance may comprise either a mixture of different components or it may be a single, pure substance.) A typical example of such use is the intraperitoneal delivery of an insulin formulation. FIG. 1 illustrates an example of this use. As shown in FIG. 1, an implantable infusion pump (IIP) 10 may be implanted in a patient below the skin and above the muscle in the abdomen. The IIP 10 will then dispense an infusion formulation (such as an insulin formulation) through the peritoneum wall 12 via a catheter 14. A lead 16 may connect IIP 10 to a sensing device (not shown) that is used to regulate the delivery of the infusion formulation.

In the case where the infusion formulation is an insulin formulation, the sensing device may regulate the delivery of the insulin formulation by sensing the levels of glucose in the patient. The delivery of the insulin formulation may then be performed in two ways. Information about the sensed glucose level may be provided to the patient (or to the patient's physician) through a communication device associated with the pump. The patient (or physician) would then manually administer an appropriate amount of the insulin formulation in accordance with the sensed glucose level. Alternatively, the sensed glucose level may be provided to a control device associated with the pump (such as a processor or other computing element) for controlling activation of the pump to deliver an appropriate amount of the insulin formulation in accordance with the sensed glucose level.

As discussed above, a typical use for an implantable infusion pump is the intraperitoneal delivery of an insulin formulation. Insulin is a protein hormone normally formed within the human pancreas. Because it regulates carbohydrate (sugar) metabolism, insulin is required for normal metabolic function. More specifically, insulin helps the body process glucose. To avoid medical problems, glucose levels should be maintained within a specific range. A normal range for glucose in the human body may be between 85 and 120 mg/dl.

In a non-diabetic person, insulin is secreted by the pancreas in small amounts throughout the day (basal rate of insulin secretion). In addition, the amount of insulin secreted by the pancreas may be modified under certain circumstances. For example, the pancreas of a non-diabetic person normally secretes larger amounts of insulin (bolus rate of insulin secretion) when the person ingests a meal to prevent postprandial hyperglycemia, i.e., abnormally increased sugar content in the blood.

In contrast to the non-diabetic person, a diabetic person's pancreas may not secrete the required amount of insulin. Thus, the diabetic person has to somehow artificially introduce the insulin into the body. One method of introducing the insulin is by the conventional insulin formulation injection method using a syringe. Using this method, the body's glucose level may be monitored (for example, by checking a blood sample) and the amount of insulin to be injected may be adjusted accordingly. For example, after a meal the glucose level may be monitored and an appropriate amount of insulin may be injected into the bloodstream of the individual.

In the alternative, a diabetic person may choose to use an infusion pump such as the implantable infusion pump described above and shown in FIG. 1. By using an infusion pump, a diabetic person may be able to adjust insulin delivery rates for the pump in accordance with the user's needs. These needs may be determined based on prior experience and/or the results of glucose monitoring (for example, by a sensing device in combination with a communication device). As an example, the basal and bolus delivery rates of an infusion pump may be adjusted in this manner.

In addition, infusion pumps may be engineered to function as an artificial pancreas. Such an infusion pump may deliver a specific amount of insulin formulation at specific intervals. As discussed above, a sensing device associated with the pump may monitor the glucose level of the user and the glucose level may then be used by the pump to automatically regulate the delivery of the insulin formulation. The automatic regulation may be carried out by a processor or other computing element associated with the pump.

The processor or other computing element may execute a closed-loop algorithm which may adjust insulin formulation delivery as a function of, for example, the rate of change over time of a sensed glucose level. These processes may be transparent to the user. Thus, the infusion pump in combination with a sensing device and closed-loop algorithm may be very beneficial to a diabetic person by automating the tasks of monitoring glucose levels and introducing an appropriate amount of insulin formulation based on the glucose level, with minimal input from the user (or the user's physician).

However, a problem exists with the method described above for the automated delivery of insulin using an infusion pump. The problem results from the fact that an individual's glucose level may be significantly affected by certain daily events. For example, when a person ingests food, glucose levels may rise due to ingested carbohydrates (sugars). In addition, it is believed that sleep affects glucose levels due to changes in the rate of glucose metabolism when a person sleeps. An individual's stress level may also affect glucose metabolism by increasing glucose levels in the bloodstream. Furthermore, the ingestion of medications may affect glucose levels within the body.

A properly functioning sensing device may detect a change in glucose level due to any of the events described above and provide the change in glucose level as an input to the closed-loop algorithm which may, in turn, provide an output to the pump to properly adjust the delivery of insulin formulation accordingly. However, in the case of an erroneous input to the closed-loop algorithm, for example, as a result of a malfunctioning sensing device, an erroneous glucose level may be indicated, leading to an erroneous adjustment in the amount of insulin delivered to the pump user. Under certain circumstances, such an error may result in extreme harm (including death) to the pump user.

Furthermore, it is believed that the body of a person merely anticipating the ingestion of a meal may have an increased level of insulin secretion. This increased insulin secretion may occur before any increase in glucose level can be detected by a sensing device. It is further believed that one reason for this leading insulin secretion reflex may be that the body is compensating, by early release of the insulin, for the time required for the insulin to react with the glucose. The secretion of insulin associated with meal anticipation is believed to lead any significant rise in glucose level by as much as 15-20 minutes. With present infusion pump systems for delivery of insulin formulation, such leading insulin secretion reflex may not be replicated, because the delivery of insulin by the pump may not occur until triggered by the detection of glucose by the sensing device.

Accordingly, there is a demand for an infusion pump system and process for delivery of insulin formulation which provides safety limits that may be used in conjunction with a closed-loop algorithm for adjusting insulin formulation delivery. The safety limits verify that levels of glucose detected by the infusion pump system's sensing device are consistent with events that may significantly affect the glucose level. In addition, there is a need for an infusion pump system and process for delivery of insulin formulation which may more accurately replicate the body's leading insulin secretion reflex.

SUMMARY OF THE DISCLOSURE

Therefore, it is an advantage of embodiments of the present invention to provide safety limits on the delivery of infusion formulation in response to a detected biological state, the safety limits being in the form of user-initiated signals corresponding to events that may significantly affect the biological state.

It is a further advantage of embodiments of the present invention to enable a user to initiate delivery of an insulin formulation before a change in a glucose level is detected in order to simulate a naturally occurring leading insulin secretion reflex.

It is a further advantage of embodiments of the present invention to provide diagnostic checks which compare an actual detected change in biological state with a change that is expected based on a user-initiated signal and alert a user to a possible malfunction when the results of the comparison are not within pre-determined limits.

It is a further advantage of embodiments of the present invention to alert a user if a detected biological state exists which should not exist in the absence of a user-initiated signal.

It is a further advantage of embodiments of the present invention to provide a user with a history of user-initiated signals, the history being accessible to the user and/or the user's physician.

These and other advantages are accomplished according to a system and process for communicating safety limits to a computing element in an infusion pump system. The safety limits may be communicated to the computing element in the form of user-initiated signals corresponding to information about events which may affect a biological state. The computing element may execute a closed-loop algorithm for adjusting the delivery of an infusion formulation base on a sensed biological state.

Preferred embodiments of the present invention provide a communication device for use with an infusion pump system for the peritoneal delivery of an insulin formulation to a diabetic user. In preferred embodiments, the communication device comprises a user interface having a plurality of user-selectable operators whereby a user may communicate information to the computing element about events that may affect a glucose level detected by a sensing device in the infusion pump system.

Depending upon the context of use, the invention may include various combinations of these features which function together to provide safety limits on the delivery of infusion formulation in response to a detected biological state. Various embodiments of the invention include one or more of these features. Preferred embodiments of the present invention contain each of these features.

These and other objects, features, and advantages of embodiments of the invention will be apparent to those skilled in the art from the following detailed description of embodiments of the invention, when read with the drawings and appended claims.

DETAILED DESCRIPTION OF EMBODIMENTS OF THE INVENTION

In the following description of preferred embodiments, reference is made to the accompanying drawings which form a part hereof, and in which is shown by way of illustration specific embodiments in which the invention may be practiced. It is to be understood that other embodiments may be utilized and structural changes may be made without departing from the scope of preferred embodiments of the present invention.

Environment of Use

Figure 1:
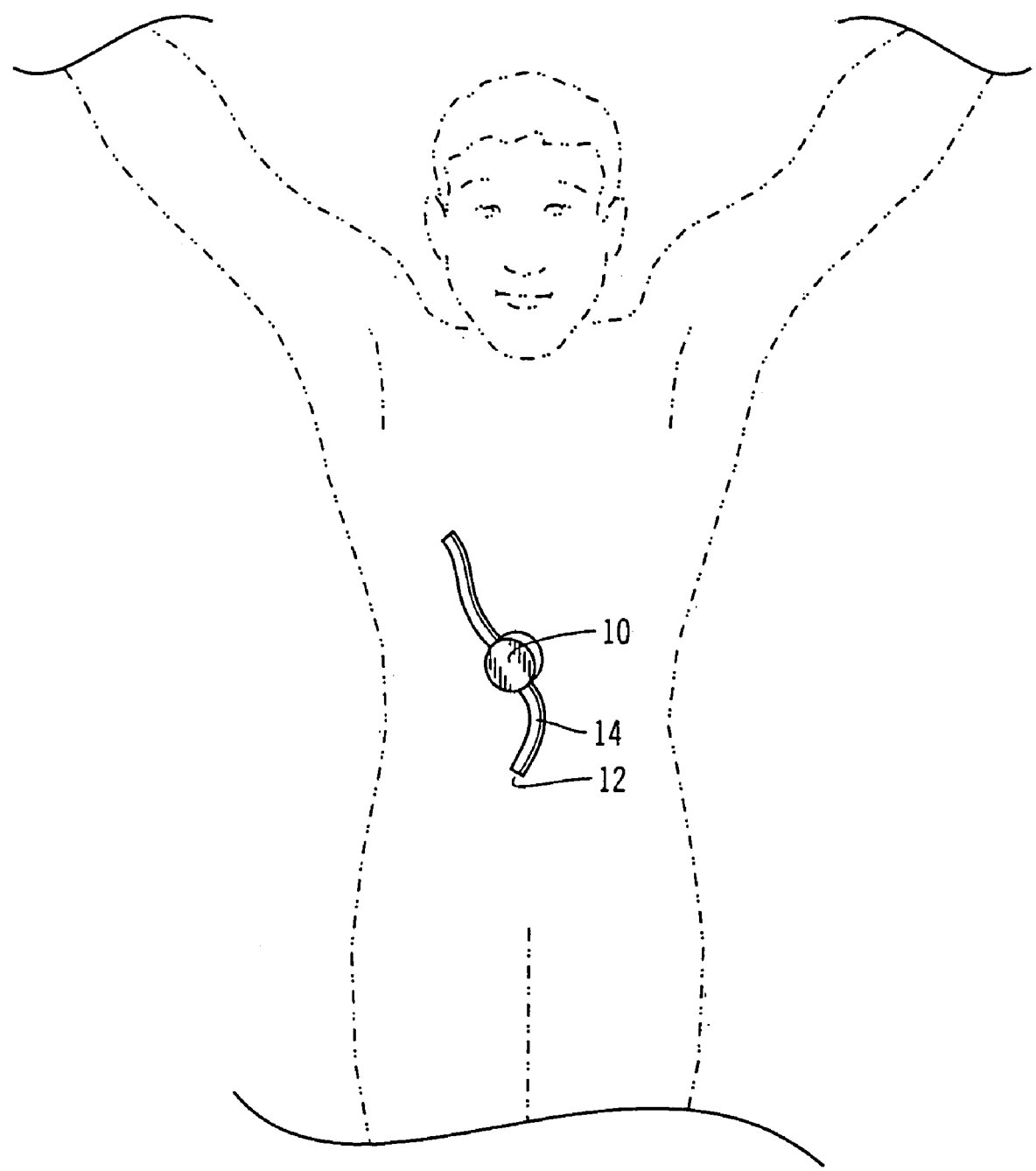
FIG. 1 shows a fragmented cutaway view of an exemplary environment of use for embodiments of the present invention in the peritoneal delivery of an insulin formulation.

As discussed above, the present invention relates generally to infusion pump systems for the delivery of infusion formulations. The invention may be employed in various infusion environments including, but not limited to a biological implant environment. In preferred embodiments, the infusion pump system and process is configured for an implant environment within a human body, as shown in FIG. 1. However, other embodiments may be employed in other biological implant or non-implant environments.

Furthermore, in preferred embodiments, the infusion pump system and process is configured for delivery of an insulin formulation used to regulate glucose levels in a diabetic user. However, other embodiments may be employed in the delivery of other infusion formulations having other pharmacological properties.

As discussed above, FIG. 1 shows IIP 10 according to an embodiment of the invention. IIP 10 may be configured to be surgically implanted into a user, for example, at a particular location in the venous system, along the spinal column, in the peritoneal cavity, or other suitable site to deliver an infusion formulation to the user. However, further embodiments of the invention may be implemented as external infusion pumps, which connect to patients through suitable catheter devices or the like.

Infusion Pump System

The infusion pump system according to preferred embodiments of the invention employs a pump for delivering measured doses of an infusion formulation. In one embodiment, the pump comprises an electromagnetic mechanism that is activated to selectively drive infusion formulation to the user. The pump may be activated according to a programmed dispensing rate or schedule, or according to an actuation signal from a sensing device, timer, manual operator or other suitable means. In one preferred embodiment, the pump may be activated by a control signal communicated to the pump from a computing element which may be included in the infusion pump system.

The infusion pump system according to preferred embodiments of the invention further employs a sensing device for monitoring a selected biological state. In one embodiment, the selected biological state to be monitored may be the glucose level detected in the body of the pump user.

The infusion pump system according to preferred embodiments of the invention further employs a computing element which may, along with other pump control functions, execute a closed-loop algorithm which may continuously adjust infusion formulation delivery as a function of the sensed biological state. In one preferred embodiment, the closed-loop algorithm may continuously adjust insulin formulation delivery as a function of the rate of change of glucose levels over time. The computing element may comprise one or more programmable processors, logic circuits, or other hardware, firmware or software components configured for implementing the control functions described herein.

The infusion pump system according to preferred embodiments of the invention further employs a communication device for communicating user-initiated signals to the computing element. The user-initiated signals may be representative of events that affect the selected biological state. In one preferred embodiment, the communication device communicates with the computing element via a radio frequency ("RF") transceiver. However, in other embodiments other suitable means of data communication may be employed, such as, for example, ultrasonics.

Events Affecting Glucose Levels

As discussed above, certain events may significantly affect glucose production levels in the human body. Thus, these events may also significantly affect the amount of insulin produced in order to metabolize the glucose. For example, the ingestion of food may significantly increase the production of glucose in the body. This results in part from the fact that during digestion carbohydrates are broken down into glucose that then enters the bloodstream.

In addition, the amount and type of foods ingested affect the amount of glucose produced.

Similarly, exercise has been shown to lower glucose levels in the human body. Thus, exercise may result in a dip in glucose levels and a corresponding decrease in the amount of insulin formulation delivered by the body. Longer or more strenuous exercise events may result in a greater dip in glucose level than shorter and less strenuous exercise events.

Furthermore, sleep and stress may affect the body's ability to burn carbohydrates and therefore may affect glucose levels. For example, glucose metabolism has been found to be slower in a sleep deprived state. In addition, elevations of certain stress hormones within the body may also result in slower glucose metabolism. Thus, longer or shorter periods of sleep or stress may result in more or less significant changes in glucose levels.

An additional event that may affect insulin production is the ingestion of medication. Certain medications may affect an individual's sensitivity to insulin, i.e. a given amount of insulin may be more or less sufficient depending on whether a particular medication has been taken. The insulin sensitivity level of a user to a particular medication may be determined either by the user or by the user's physician, for example, by observing the user's glucose level after taking a particular medication.

Closed-Loop Algorithm Safety Limits

An infusion pump system for the automatic regulation of the delivery of insulin formulation should detect changes in glucose levels that may result from any of these events and adjust the amount of insulin formulation delivered accordingly. In an exemplary infusion pump system for the automatic regulation of the delivery of insulin formulation, a sensing device used in conjunction with the infusion pump may detect changes in the glucose level and provide this information as an input to a closed-loop algorithm. The typical closed-loop algorithm may then accordingly adjust the amount of insulin formulation delivered to the user.

However, dangers exists in the typical infusion pump system for the automatic regulation of the delivery of insulin formulation. One of the dangers is that the input to the closed-loop algorithm may be erroneous. In typical existing infusion pump systems for the automatic regulation of the delivery of insulin formulation, there may be no safety limits on the amount of insulin formulation that is delivered based on an erroneous input. In other words, the typical closed-loop algorithm may only examine the glucose level input and may have no way to verify whether the change in glucose level is a reasonable change, i.e., one that is consistent with an event affecting glucose levels.

Furthermore, as discussed above, the human body shows evidence of a leading insulin secretion reflex in response to anticipation of the ingestion of a meal. Typical existing infusion pump systems for the automatic regulation of the delivery of insulin formulation may not replicate this reflex, because the delivery of insulin formulation by the pump may not occur until triggered by the detection of glucose by the sensing device.

Therefore, according to preferred embodiments of the infusion pump system and process, the communication device comprises a user interface for entering user-initiated signals representative of events which may affect glucose levels in a biological system such as the human body. The user-initiated signals are provided to a computing element within the system which executes a closed-loop algorithm for adjusting insulin formulation delivery as a function of, for example, the rate of change over time of a sensed glucose level.

Figure 2:
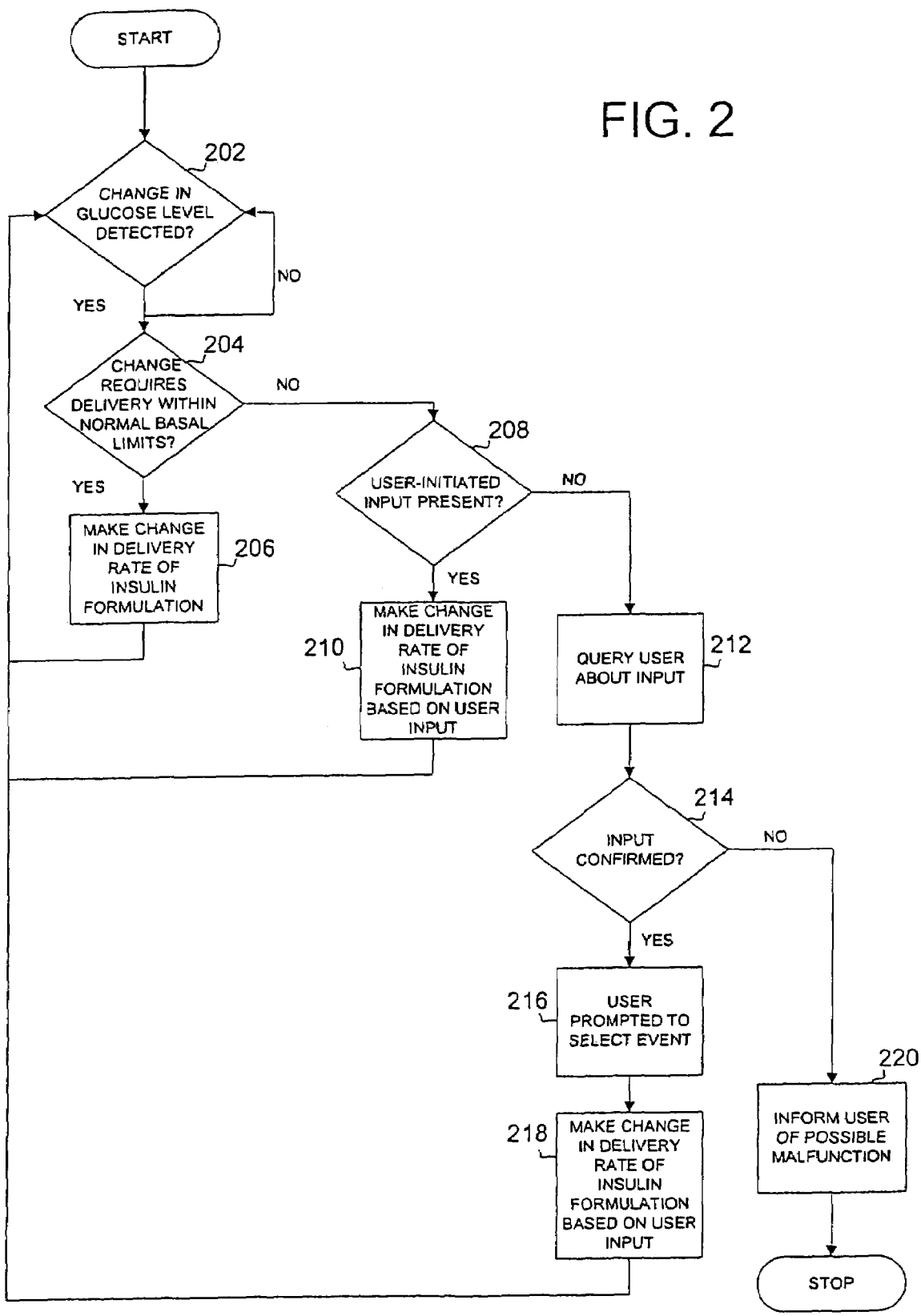
FIG. 2 shows a flowchart of a closed-loop algorithm for adjusting insulin formulation delivery as a function of the rate of change over time of a sensed glucose level and/or a user-initiated signal according to an embodiment of the invention.

FIG. 2 shows a flowchart of a closed-loop algorithm for adjusting insulin formulation delivery as a function of the rate of change over time of a sensed glucose level which incorporates one embodiment of the invention's system and process. As shown in step 202, the closed-loop algorithm may continuously check for changes in glucose level. A sensing device may detect the change in glucose level and may communicate the change to the computing element as a glucose level input to the algorithm. If no change is detected, the closed-loop algorithm may loop back to step 202, repeating this process until a change is detected. When a change occurs, the closed-loop algorithm may determine whether the amount of insulin formulation required based on the change in glucose level is within normal basal limits for the user, as shown in step 204.

The normal basal limits for the user may have been pre-programmed into the algorithm by the user or the user's physician. The normal basal limits may include maximum and minimum values of insulin formulation that may be delivered at one time. For example, if the user is in a basal state (i.e., a state requiring a basal rate of insulin secretion), the closed-loop algorithm may limit the delivery of insulin formulation to a maximum of fifty percent higher than a pre-programmed nominal basal rate of delivery. Similarly, the closed-loop algorithm may not allow the delivery rate to drop below a minimum allowable rate, for example, 0.2 units per hour.

Furthermore, the user (or the user's physician) may pre-program a user's basal profile into the closed-loop algorithm. This basal profile may indicate to the closed-loop algorithm, for example, that the user has a lower need for insulin at night.

Referring again to FIG. 2, if the change in glucose level requires an amount of insulin formulation that is within the pre-programmed basal limits and profile, the closed-loop algorithm may make a suitable adjustment to the delivery rate, as shown in step 206. The closed-loop algorithm may then loop back to step 202, repeating steps 204 through 206 described above.

However, if the detected change in glucose level requires the delivery of an amount of insulin formulation not within the basal limits or profile of the user, the closed-loop algorithm may scan "event inputs" to the closed-loop algorithm in order to determine if a user-initiated signal is present, as shown in step 208. If a user-initiated signal is present, the closed-loop algorithm may then process the signal to determine the adjustment in the insulin formulation delivery rate that corresponds to the user-initiated signal that is present at the event input, as shown in step 210.

On the other hand, in one embodiment, if no user-initiated signal is present at the event input to the closed-loop algorithm, the user may be queried, for example, via the communication device user interface, whether an event has occurred which requires the user to communicate a signal to the computing element, as shown in step 212. The communication device user interface may include user-selectable responses to the query.

If the user confirms that an event has occurred, as shown in step 214, the user may then be prompted to select the event, as shown in step 216. Once the user-initiated signal corresponding to the selected event is received at an event input of the closed-loop algorithm. The closed-loop algorithm may then process the signal to determine the adjustment in the insulin formulation delivery rate that corresponds to the user-initiated signal that is present at the event input, as shown in step 218.

In one preferred embodiment, if the user does not confirm that an event requiring an insulin formulation delivery amount outside of the pre-programmed basal limits has occurred, the closed-loop algorithm may alert the user to a possible malfunction in the infusion pump system, as shown in step 220. The closed-loop algorithm may then cease automatic control of the infusion pump and return to a manual operation so that the user or the user's physician may control the delivery rate.

Furthermore, in one preferred embodiment, the closed-loop algorithm may be programmed to perform diagnostic checks to ensure that a user-initiated signal communicated to an event input of the closed-loop algorithm is consistent with the glucose level detected by the sensing device. For example, if the user enters a meal event and the sensing device does not detect a corresponding change in the glucose level within a pre-programmed time, the closed-loop algorithm may alert the user to a possible malfunction in the infusion pump system. The closed-loop algorithm may then cease automatic control of the infusion pump and return to a manual operation so that the user or the user's physician may control the delivery rate.

As shown by the flowchart in FIG. 2, embodiments of the invention's system and process advantageously incorporates safety limits into the closed-loop algorithm to ensure that insulin formulation delivery amounts outside of a pre-programmed normal basal delivery rate correspond to events which may significantly affect glucose level. These events may be communicated by the user to the closed-loop algorithm event inputs via a communication device user interface. In one preferred embodiment, the events that may significantly affect glucose levels may comprise, for example, a meal event, an exercise event, a sleep event, a stress event, and a medication event.

Communication Device User Interface

The events may be communicated by the user to the closed-loop algorithm event inputs via a communication device user interface. User-selectable operators may be provided on the communication device user interface which allow a user to initiate a signal representing an event.

Thus, for example, the user may be able to press or otherwise select a user-selectable operator representing a sleep event before the user sleeps. In preferred embodiments, the closed-loop algorithm accepts the user-initiated signal at an event input and verifies that the glucose level input provided by the sensing device is consistent with the presence of the user-initiated signal at the event input of the closed-loop algorithm, as described above in relation to FIG. 2.

In one preferred embodiment, a user-initiated signal may initiate changes in the delivery amount of the infusion formulation independently of the sensing device input. For example, in one embodiment, a user may select a "meal" user-selectable operator on the user interface when the user is about to consume a meal. The user-initiated signal corresponding to the meal event communicated to the computing element may then initiate an immediate bolus delivery of insulin formulation by the pump even though the sensing device has not yet detected any rise in the glucose level.

Thus, the naturally occurring leading insulin secretion reflex phenomenon may be advantageously replicated by preferred embodiments of the infusion pump system and process by programming the closed-loop algorithm to deliver a suitable amount of insulin formulation based on the signal initiated by the user selecting the "meal" user-selectable operator, without the sensing device detecting any rise in glucose level.

In other preferred embodiments, the user interface may comprise user-selectable operators for selecting an "event ranking," for example, a degree, quantity, or measure of the selected event. As an example, if the user has selected a meal event, the user may be able to supplement this event information by selecting the size of the meal, for example, "light," "moderate," or "heavy." In addition, in some preferred embodiments, the user may be able to further supplement the event information by entering dietary information about the meal. For example, the user may be able to enter the meal's carbohydrate content, fat content, or other dietary information about the meal to be consumed. This information may be used to more accurately determine the expected effect of the meal on the glucose level.

In yet other preferred embodiments, if the user initially inputs one size for a meal but later decides to eat more or less, the user may be able to update the meal information although delivery of the insulin formulation by the infusion pump is already in progress based on the initial input. This may be done, for example, by selecting and inputting the event ranking which corresponds to the new size of the meal. In this embodiment, the computing element may dynamically (i.e. while delivery is in progress) re-calculate the amount of insulin formulation delivered based on both inputs.

As an example of this embodiment, the user may first select a light meal and input a corresponding signal. Then, after delivery is in progress, the user may decide that a heavy meal is preferable. The user may then select and input the event ranking which corresponds to a heavy meal. The computing element may then dynamically adjust the amount of insulin formulation delivered based on both the light and heavy inputs.

Similarly, the user interface may comprise user-selectable operators for selecting an event ranking for an exercise event. As an example, if the user has selected an exercise event, the user may be able to supplement this event information by selecting the type of exercise, the duration of the exercise, and/or whether the exercise is "light," "moderate," or "heavy."

In addition, the user interface may comprise user-selectable operators for selecting an event ranking for a sleep event. As an example, if the user has selected a sleep event, the user may be able to supplement this event information by selecting the amount of time the user expects to sleep.

Alternatively, the user may select an event ranking such as, but not limited to, "short," "moderate," or "long," corresponding to a short, moderate, or long interval of sleep. As an additional example, the user may simply press a "sleep" user-selectable operator before the sleep event and a "wake" user-selectable operator when the user awakes. In addition, or in the alternative, some preferred embodiments may enable the user to enter a time when the user expects to wake and the computing element may automatically calculate the duration of the sleep event and adjust the amount of delivered insulin formulation accordingly.

The user interface may further comprise user-selectable operators for selecting an event ranking for a stress event. As an example, if the user has selected a stress event, the user may be able to supplement this event information by selecting the ranking of stress, for example, "light," "moderate," or "heavy."

Furthermore, the user interface may comprise user-selectable operators for selecting an event ranking for a medication event. As an example, if the user has selected a medication event, the user may be able to supplement this event information by selecting the type of medication and/or the amount of the medication.

Alternatively, the user interface may comprise user-selectable operators which enable the user to, for example, simply select a level of sensitivity to insulin that is associated with the ingestion of a particular medication. A particular user's insulin sensitivity level associated with the ingestion of a particular medication may have been previously determined either by the user or by the user's physician. For example, a particular user's insulin sensitivity level may have been previously determined by observing the user's glucose level after taking the medication. Thus, the medication event ranking may be, for example, "low," "moderate," or "high," corresponding respectively to a low, moderate, or high sensitivity to insulin after taking a particular medication.

In one embodiment, the user-initiated signals are communicated to the computing element where they may be provided as an input to the closed-loop algorithm. The closed-loop algorithm may then incorporate the user-initiated signals into the algorithm's calculation of insulin formulation output, as described in reference to FIG. 2.

Figure 3:
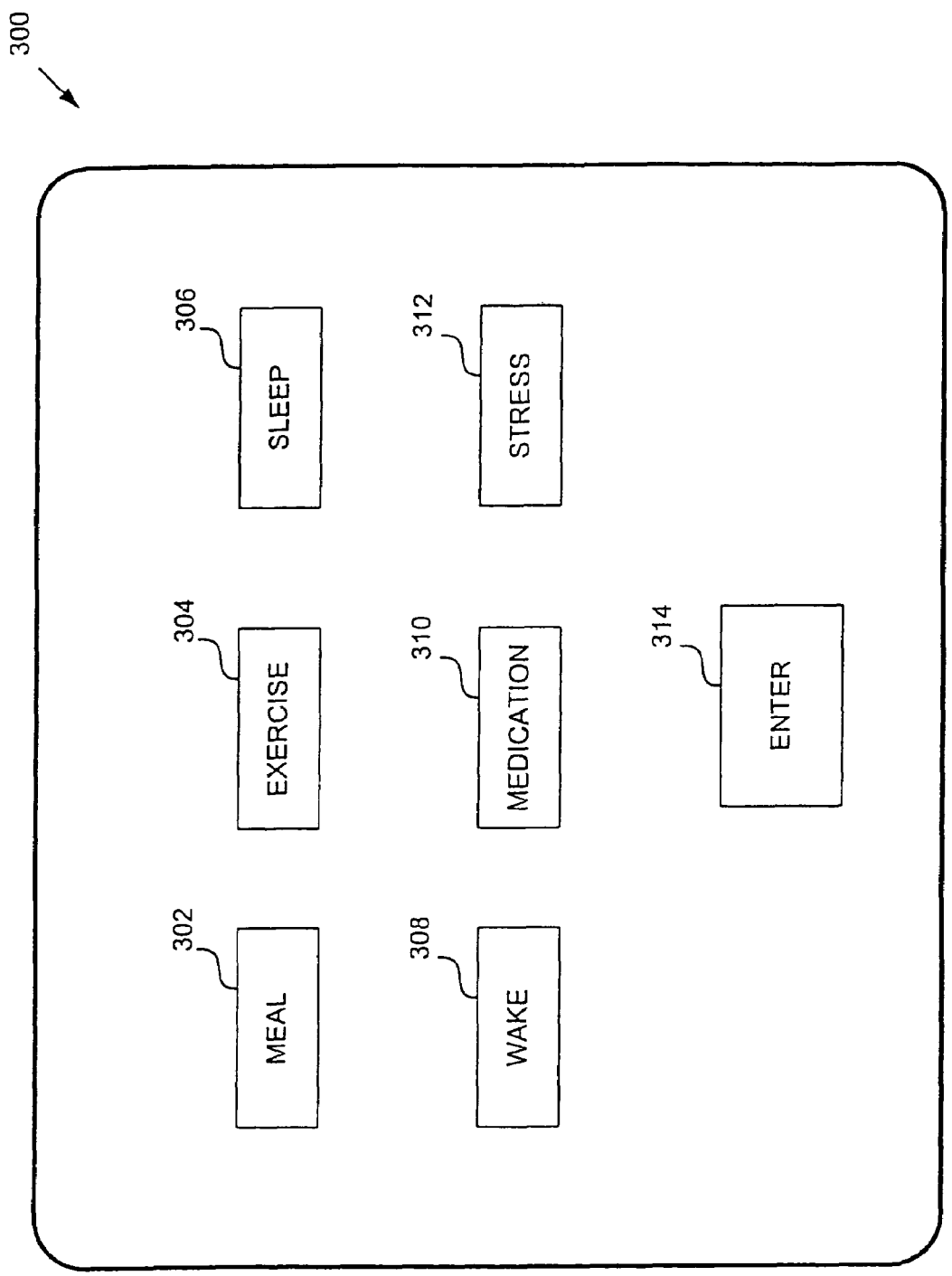
FIG. 3 shows an exemplary communication device user interface comprising a plurality of user-selectable operators corresponding to particular events, according to an embodiment of the invention.

FIG. 3 illustrates an example of a communication device user interface according to one preferred embodiment. In preferred embodiments, the communication device 300 is provided with a power source, for example, a battery, independent of the infusion pump power source. In other embodiments, the communication device 300 may be powered from the infusion pump power source.

Communication device 300 comprises an outer case or housing. This case or housing may be plastic, metal, or any other suitable material. Situated on the outer housing is the user interface. In the present preferred embodiment, the user interface comprises a plurality of user-selectable operators, each of the plurality of user-selectable operators corresponding to a particular event. Thus, communication device 300 comprises a simple user interface which enables a user to select an event simply by pressing or otherwise selecting the corresponding user-selectable operator.

In one preferred embodiment, the user may confirm the selection of an event by selecting an "enter" user-selectable operator 314. The inclusion of the "enter" user-selectable operator 314 may provide a measure of safety against accidental selection of an event user-selectable operator by, for example, bumping the communication device against another object. Thus, both the user-selectable operator corresponding to the desired event and the "enter" user-selectable operator 314 must be depressed in succession in order for a signal to be communicated to the computing element. In another embodiment, a confirmation screen may be used for a particularly important event, such as, for example, delivering a bolus. For example, upon the entering of a large meal event, the screen may respond by displaying "Large Meal Entered. Confirm?" Then, the user may depress enter again to confirm the event. This operation provides an extra level of safety.

In other embodiments, the "enter" user-selectable operator may be absent and other safety measures used against accidental selection. For example, in one embodiment, the user-selectable operators may be situated in a recessed portion of the communication device housing in order to avoid accidental selection. The user may be provided with a selection device, for example, a wand or pointer device, in order to access the user-selectable operators. In yet other embodiments, both safety measures may be employed.

In the embodiment of the communication device user interface shown in FIG. 3, a user may select the "meal" user-selectable operator 302 and then select the "enter" user-selectable operator 314 in order to communicate a signal to the computing element that the user is about to ingest a meal or is currently ingesting a meal. The closed-loop algorithm may then receive the user-initiated signal as an event input. In preferred embodiments, the computing element may confirm that the user-initiated signal was received, for example, by beeping, displaying a "signal received message," or other suitable method of informing the user that the computing element has received the signal.

Similarly, the user may select user-selectable operators 304, 306, 308, 310, or 312 in order to select the "exercise," "sleep," "wake," "medication," and "stress" events, respectively, and then select the "enter" user-selectable operator 314 in order to communicate the respective signal to the computing element that the user is about to exercise, is about to sleep, is now awake after sleeping, has taken medication, or is experiencing stress.

The embodiment of the communication device user interface shown in FIG. 3, advantageously provides the user with a user-friendly interface for communicating event information to the computing element. The amount of event information communicated to the computing element is kept to a minimum. However, embodiments of the infusion pump system and process may advantageously use even this minimal amount of event information to provide safety limits to insulin formulation delivery. For example, in one preferred embodiment using the communication device user interface shown in FIG. 3, the user's physician may be provided with password-protected access to the user's communication device in order to modify the closed-loop algorithm in accordance with parameters specific to the user.

As an example, a physician may determine the impact that taking a particular medication may have on the user's insulin sensitivity. The physician may then program the closed-loop algorithm in such a way that when the event input to the closed-loop algorithm receives a user-initiated signal corresponding to the "medication" user-selectable operator 310, the closed-loop algorithm may adjust the insulin formulation delivery in accordance with the physician's programmed instructions.

Similarly, the physician may modify the closed-loop algorithm to respond in a particular way to the selection by the user of user-selectable operators corresponding to other events. In addition, in some preferred embodiments, the computing element may maintain a history of user-initiated events that may be accessed by the user and/or the physician. For example, a history of the pump user's "meal" events may be maintained and accessed by the physician. The physician may advantageously use this information to advise the user on, for example, lifestyle patterns that may be affecting the user's health and well-being.

Figure 4:
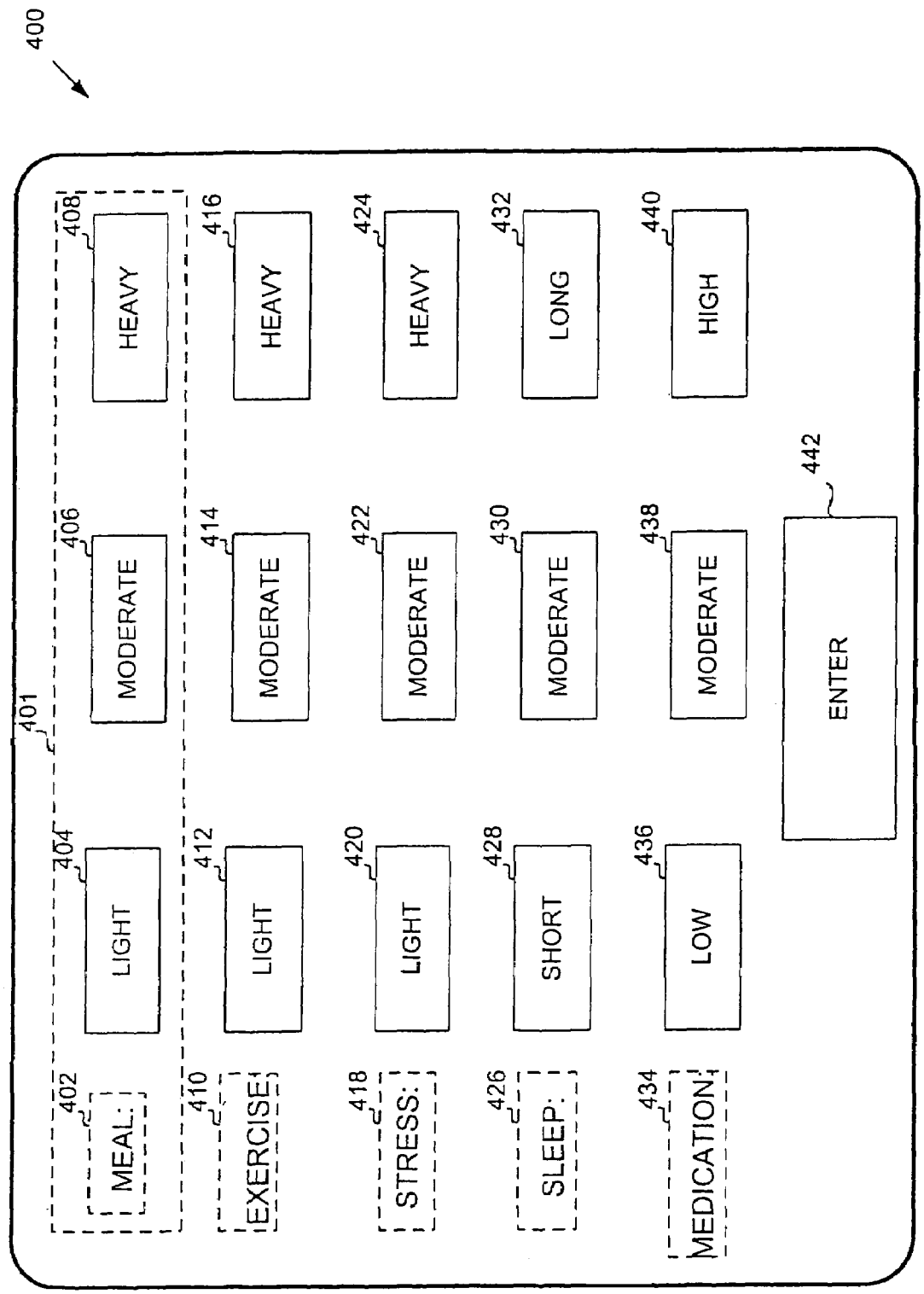
FIG. 4 shows an exemplary communication device user interface comprising a plurality of user-selectable operators for selecting various event rankings corresponding to particular events, according to an embodiment of the invention.

FIG. 4 illustrates an example of a communication device user interface according to another preferred embodiment. Communication device 400 is provided with a power source, for example, a battery, independent of the infusion pump power source. In other embodiments, the communication device 400 may be powered from the infusion pump power source.

Communication device 400 comprises an outer case or housing. This case or housing may be plastic, metal, or any other suitable material. Situated on the outer housing is the user interface. In the present preferred embodiment, the user interface comprises a plurality of user-selectable operators for selecting various event rankings corresponding to particular events. The events may be indicated on the communication device 400 user interface by printed words, pictures, or other indicia representing the event. As an example, in FIG. 4, the events are indicated vertically along the left side of the communication device 400 user interface as "meal" 402, "exercise" 410, "stress" 418, "sleep" 426, and "medication" 434.

Event rankings associated with each event are situated to the right and in the same row as the associated event. In the embodiment shown in FIG. 4, the event indicators are not selectable but merely indicate the event associated with the user-selectable operators located in that particular row. For example, "meal" 402 event indicator is not selectable, but merely indicates that event rankings "light" 404, "moderate" 406, and "heavy" 410, located in the row indicated by reference numeral 401, are event rankings associated with the "meal" 402 event.

Similarly, event rankings "light" 412, "moderate" 414, and "heavy" 416 are event rankings associated with the "exercise" 410 event; event rankings "light" 420, "moderate" 422, and "heavy" 424 are event rankings associated with the "stress" 418 event; event rankings "short" 428, "moderate" 430, and "long" 432 are event rankings associated with the. "sleep" 426 event; and event rankings "low" 436, "moderate" 438, and "high" 440 are event rankings associated with the "medication" 434 event.

In addition to the event ranking user-selectable operators described above, the communication device 400 user interface also comprises an "enter" user-selectable operator 442 which operates in a manner similar to that of "enter" user-selectable operator 314 described above in relation to FIG. 3.

In the embodiment of the communication device 400 user interface shown in. FIG. 4, the user is able to enter more detailed information about a particular event than was the case for the communication device 300 user interface, shown in FIG. 3. As an example, for a "meal" event the user may locate the row on the communication device 400 user interface that has the "meal" 402 indicator. To the right of the "meal" 402 indicator there are three event rankings associated with the "meal" event, "light" 404, "moderate" 406, and "heavy" 408. These event rankings correspond, generally, to a light meal, a moderate meal, and a heavy meal, respectively.

Although in the embodiment shown in FIG. 4 there are three event rankings associated with each event, other embodiments may have more or less than three event rankings associated with a particular event. Furthermore, although in the embodiment shown in FIG. 4 certain event rankings are associated with a particular event, other event rankings are also possible in other embodiments. For example, although in the embodiment shown in FIG. 4 the event rankings associated with a meal event are light, moderate, and heavy, in other embodiments the event ranking descriptions may comprise more accurate quantitative descriptions. For example, in one embodiment, the event rankings associated with the meal event could be "less than X grams of carbohydrates," and "more than X grams of carbohydrates." The effects for a particular user of selecting any one of these event ranking user-selectable operators may be pre-programmed into the closed-loop algorithm and may, in some embodiments, be modified by a user's physician as described above in relation to FIG. 3.

Figure 5:
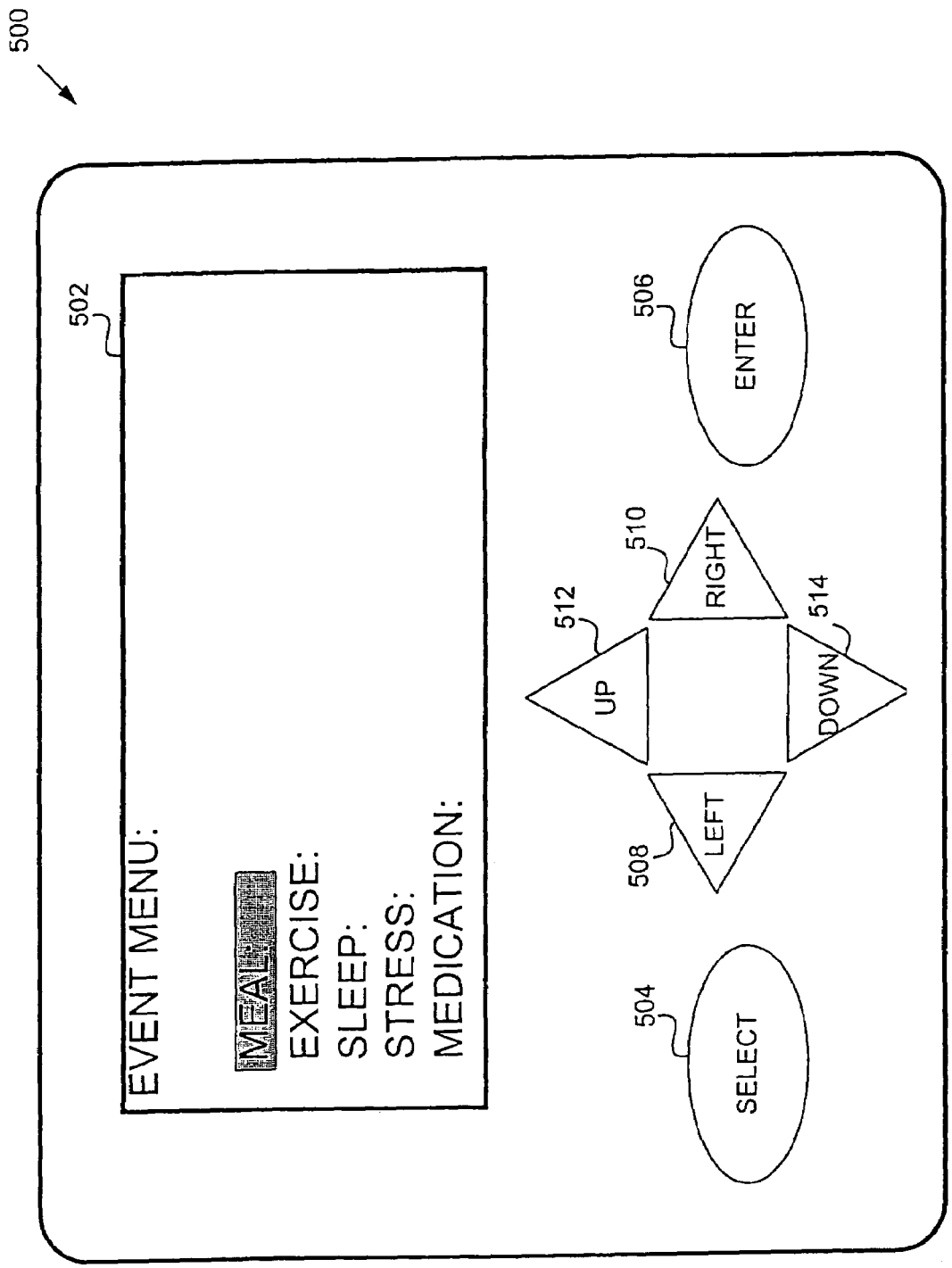
FIG. 5 shows an exemplary communication device user interface comprising a display for displaying events and event ranking information to a user, along with user-selectable operators for selecting and entering the events and event ranking information, according to an embodiment of the invention.

FIG. 5 illustrates an example of a communication device user interface according to another preferred embodiment. Communication device 500 is provided with a power source, for example, a battery, independent of the infusion pump power source. In other embodiments, the communication device 500 may be powered from the infusion pump power source.

Communication device 500 comprises an outer case or housing. This case or housing may be plastic, metal, or any other suitable material. Situated on the outer housing is the user interface. In the present preferred embodiment, communication device 500 user interface comprises display 502, "select" user-selectable operator 504, "enter" user-selectable operator 506, "cursor left" user-selectable operator 508, "cursor right" user-selectable operator 510, "cursor up" user-selectable operator 512, and "cursor down" user-selectable operator 514.

Display 502 may comprise any electronic display device for representing images and text. Display 502 may comprise, for example, a liquid crystal display ("LCD"), a thin film transistor ("TFT"), or any other type of suitable display device. Communication device 500 user interface may enable the user to display particular information on display 502 by selecting the "select" user-selectable operator 504 either alone or in combination with one or more other user-selectable operators.

For example, by initially selecting "select" user-selectable operator 504, a menu of events may be displayed to the user, as shown in FIG. 5. The user may then scroll through events on the menu by, for example, using the cursor user-selectable operators 508, 510, 512, and 514. The cursor highlights the currently selected event. In FIG. 5, the currently selected event is the "meal" event. In one preferred embodiment, once the desired event is highlighted, the user may then select the "enter" user-selectable operator 506 to proceed, for example, to an event ranking menu, as displayed in display 602, shown in FIG. 6.

Figure 6:
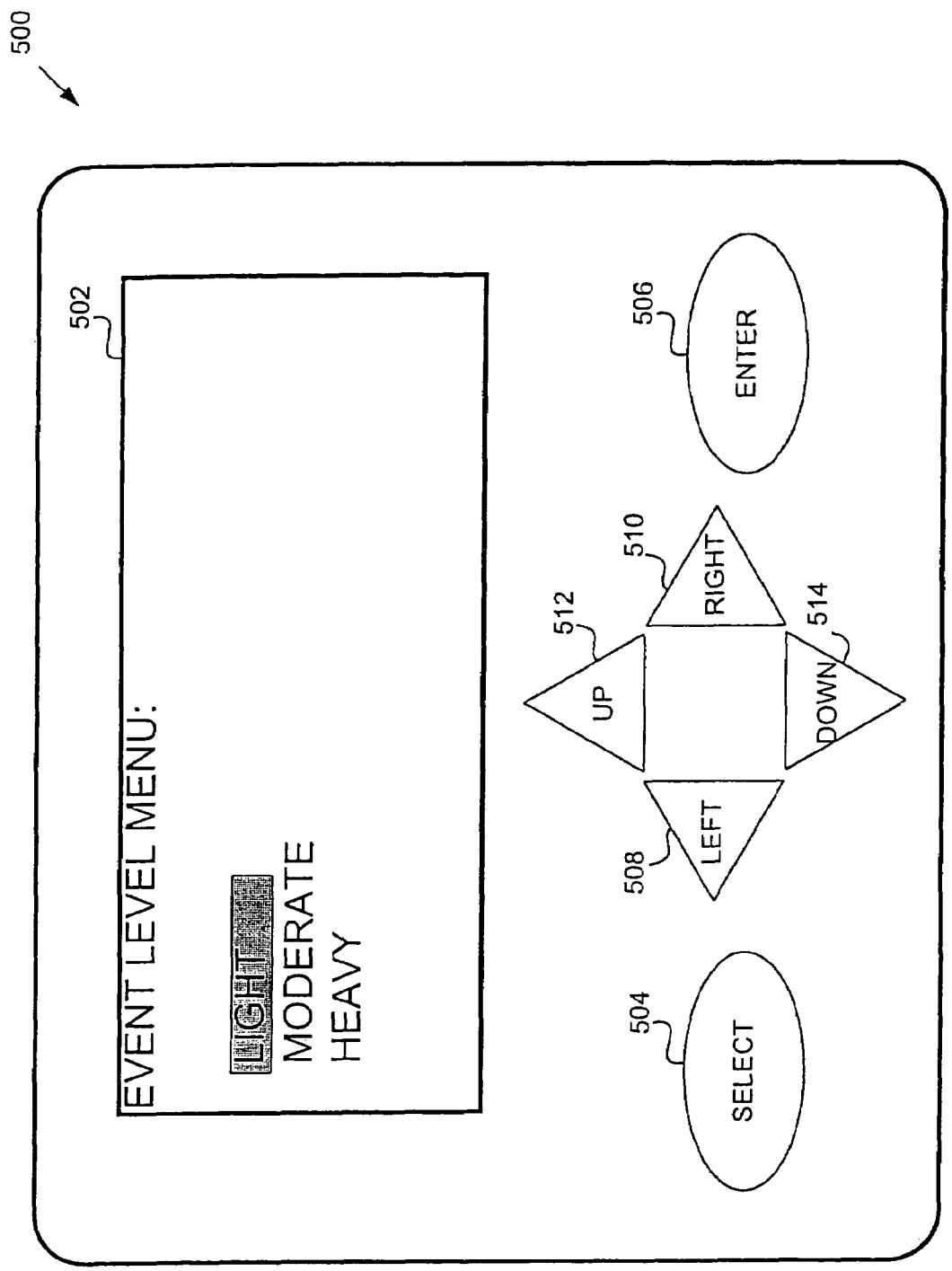
FIG. 6 shows an exemplary communication device user interface comprising an event ranking selection screen, according to an embodiment of the invention.

FIG. 6 shows an event ranking selection screen on display 502 of the communication device 500 user interface. Assuming that the user selected the meal event, the event rankings associated with the "meal" event are displayed on display 502. In one preferred embodiment, these event rankings are "light," "moderate," and "heavy." The user may then scroll through the displayed event rankings on the menu by, for example, using the cursor user-selectable operators 508, 510, 512, and 514. The cursor highlights the currently selected event ranking. In FIG. 6, the currently selected event ranking is the "light" event ranking. In one preferred embodiment, once the desired event ranking is highlighted, the user may then select, for example, the "enter" user-selectable operator 506 or the "select" user-selectable operator 504 to communicate a signal corresponding to the selected event ranking to the computing element.

Figure 7:
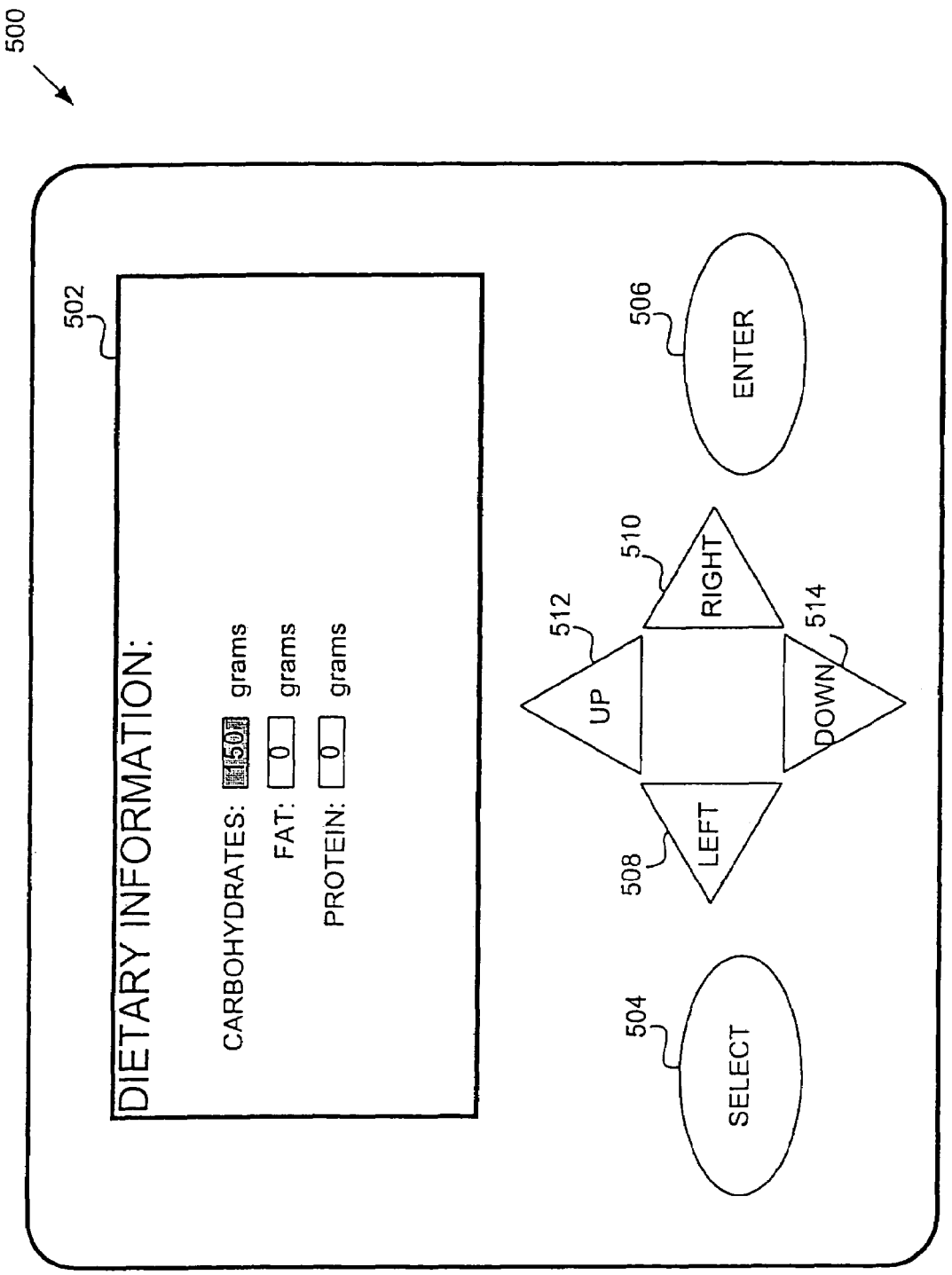
FIG. 7 shows an exemplary communication device user interface comprising a display for entering detailed dietary information about a meal event, according to an embodiment of the invention.

FIG. 7 shows another embodiment of the communication device 500 user interface wherein more detailed information may be entered regarding the meal event. In the embodiment of the communication device 500 user interface shown in FIG. 7, particular dietary substances and/or compounds may be displayed to the user in display 502. The user may enter an amount for each substance and/or compound. The amount may be expressed in a suitable unit of measurement, for example in grams. As an example, the user may use the cursor user-selectable operators 508, 510, 512, and 514 to highlight a particular substance or compound. The user may then select, for example, the "select" user-selectable operator 504 to select the substance or compound currently highlighted.

The user may then use, for example, the "cursor up" user-selectable operator 512 and "cursor down" user-selectable operator 514 to either increase or decrease, respectively, the displayed units of measurement. When the user has entered the dietary information, the user may select the "enter" user-selectable operator 506 in order to communicate the dietary information to the computing element.

Figure 8:
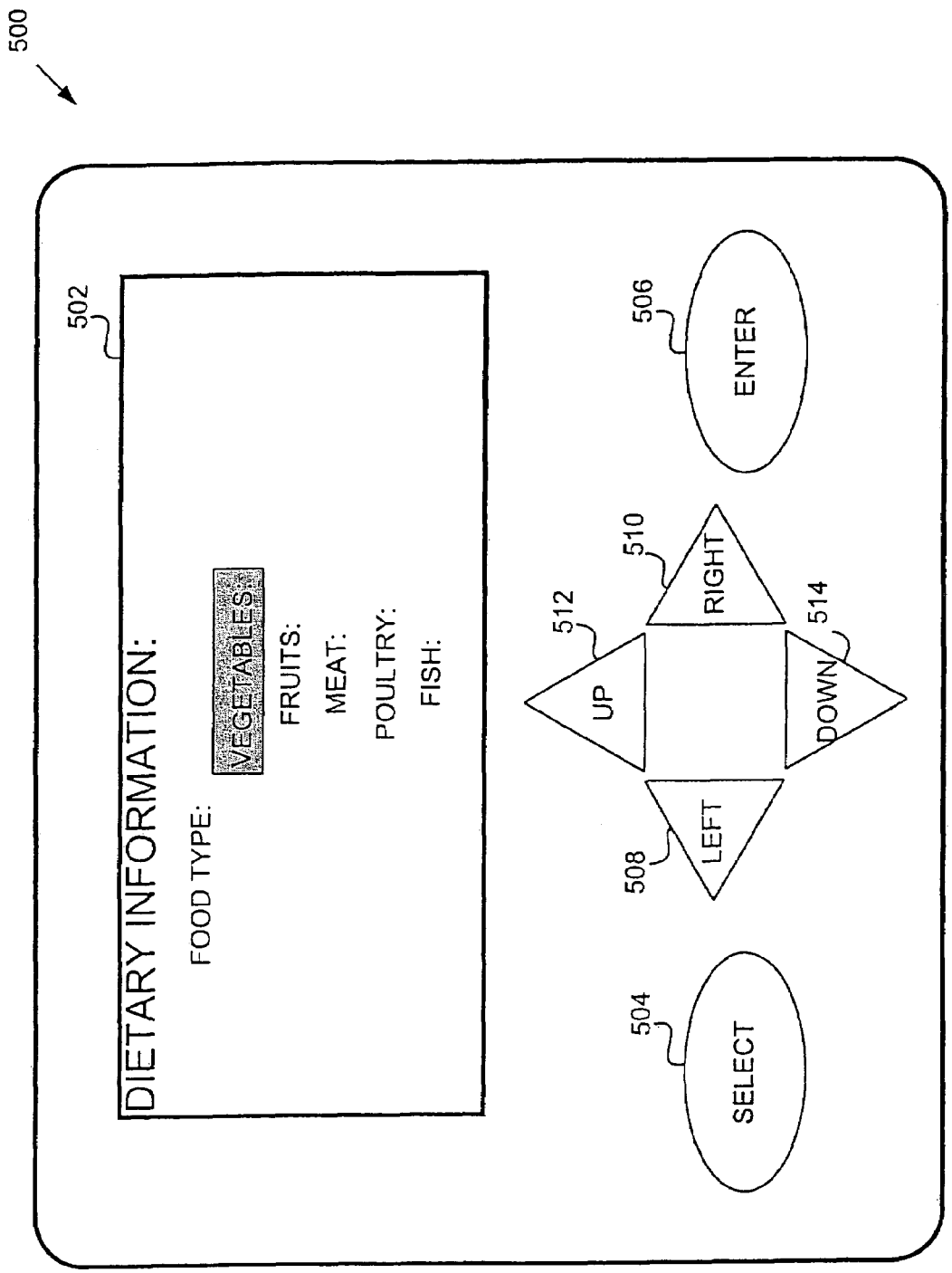
FIG. 8 shows an exemplary communication device user interface comprising a display for displaying a menu of selectable food types, according to an embodiment of the invention.

In yet other preferred embodiments, the user may select foods from food menus, as shown in FIG. 8. In one preferred embodiment, a menu of selectable food types may be displayed to the user in display 502 of the communication device 500 user interface after the meal event has been selected by the user. The user may then use the cursor user-selectable operators 508, 510, 512, and 514 to highlight a particular food type. In FIG. 8, the user has highlighted the "vegetable" food type. The user may then select, for example, the "select" user-selectable operator 504 or the "enter" user-selectable operator 506 in order to select the food type currently highlighted.

Figure 9:
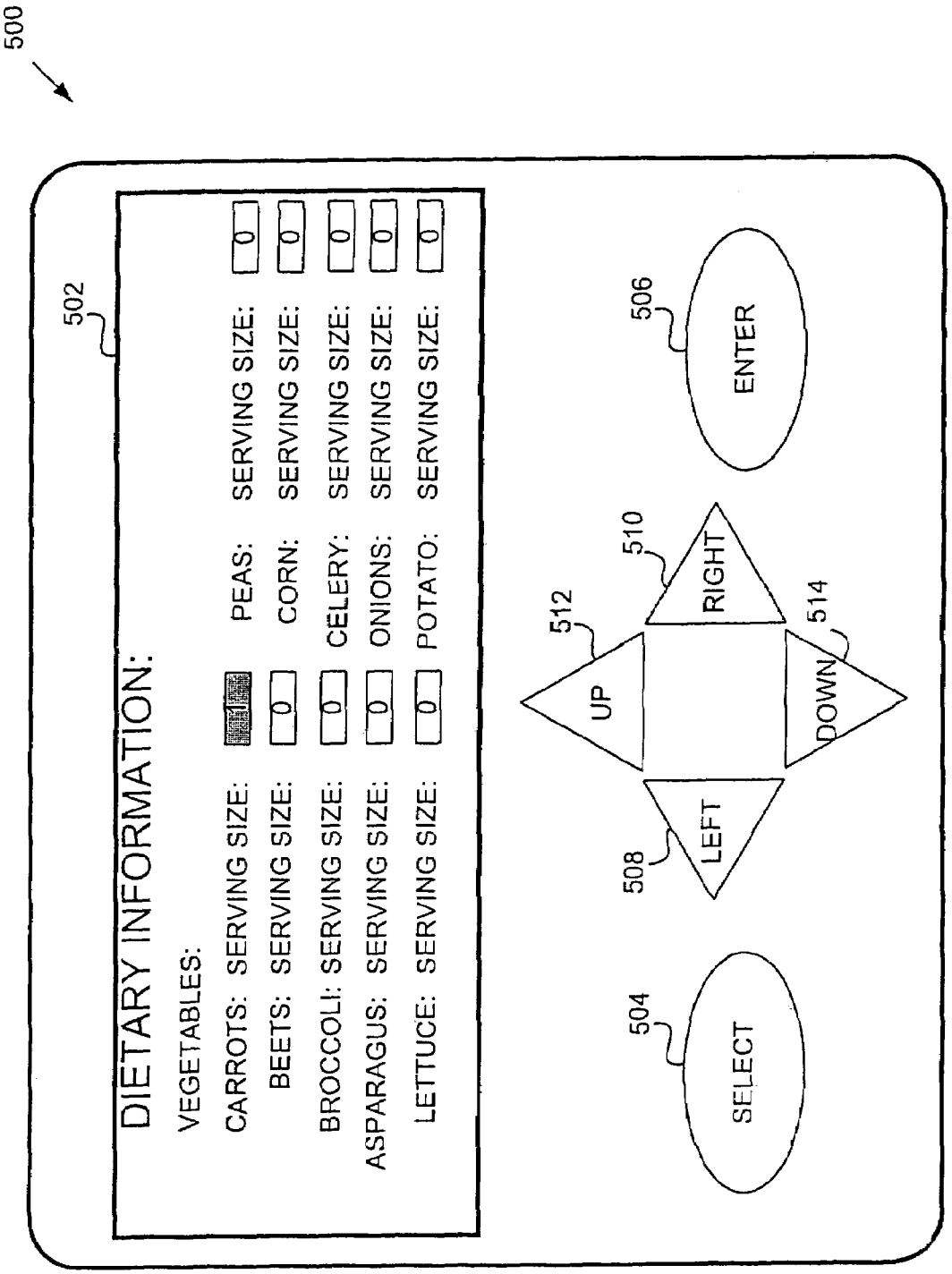
FIG. 9 shows an exemplary communication device user interface comprising a display for displaying a menu of foods corresponding to a selected food type, according to an embodiment of the invention.

In one preferred embodiment, when the currently highlighted food type is selected, a menu of foods corresponding to that food type may be displayed to the user, as shown in FIG. 9. FIG. 9 shows a selectable menu of vegetables in display 502. The user may use the cursor user-selectable operators 508, 510, 512, and 514 to highlight a particular vegetable. In one embodiment, the user may then use, for example, the "cursor up" user-selectable operator 512 and "cursor down" user-selectable operator 514 to either increase or decrease, respectively, the displayed number of serving sizes. Once the number of serving sizes has been selected, the user may then select, for example, either the "enter" user-selectable operator 506 or the "select" user-selectable operator 504 in order to communicate the dietary information to the computing element.

In preferred embodiments of the communication device 500 user interface shown in FIGS. 8 and 9, information about a particular food, such as, but not limited to, grams of fat per serving, grams of carbohydrates per serving, and grams of protein per serving, may be stored in a storage device located, for example, either in the computing element or within the communication device 500 itself. Thus, when a user selects a particular food and serving size, the dietary information may be calculated automatically by the computing element using the previously stored information. The closed-loop algorithm may then advantageously use this dietary information to more accurately determine the amount of insulin formulation to deliver.

Therefore, embodiments of the invention's infusion pump system and process provide a communication device user interface for entering user-initiated signals for communication to a computing element within the system. The user-initiated signals may be provided as event inputs to a closed-loop algorithm executed by a computing element. When the system's sensing device detects changes in a biological state, the closed-loop algorithm may be programmed to verify that an event input is present before delivering an amount of infusion formulation outside of pre-programmed basal limits.

The amount of insulin formulation to be delivered based on a particular event may be determined by pre-programmed data concerning the user. This pre-programmed data may be entered, for example, by the user and/or the user's physician or other medical professional. Thus, the event inputs provide safety limits to the amount of infusion formulation delivered in response to changes in a particular biological state.

Accordingly, a number of aspects and features of preferred embodiments of the communication device user interface described above may provide individually, or may be combined to provide user-initiated signals to a computing element within an infusion pump system. However, the foregoing description of preferred embodiments of the invention has been presented for the purposes of illustration and description. It is not intended to be exhaustive or to limit the invention to the precise forms disclosed. Many modifications and variations are possible in light of the above teaching.

For example, the events described above in preferred embodiments of the invention's system and process are examples of events which may lead to changes in insulin production by the pancreas of a non-diabetic person, and for which a user-initiated signal may be provided to a closed-loop algorithm. However, the above-named events should not be considered to be a limitation on the events which may affect glucose levels in the human body, and thus on the events for which a user-initiated signal may be provided to the closed-loop algorithm by embodiments of the invention's system and process.

Having disclosed exemplary embodiments and the best mode, modifications and variations may be made to the disclosed embodiments while remaining within the scope of the invention as defined by the following claims.

What is claimed is:

1. An infusion pump system for use in delivery of an infusion formulation, the system comprising:
    a pump for delivering measured doses of an infusion formulation;
    a sensing device for sensing a biological state;
    a computing element communicating with the sensing device, the computing element being programmed to receive information about the sensed biological state from the sensing device and to regulate the delivery of the infusion formulation in accordance with the received information; and
    a communication device communicating with the computing element, the communication device for communicating a user-initiated event signal to the computing element, the user-initiated event signal being representative of an event affecting the sensed biological state;
    wherein the computing element is further programmed to determine whether an amount of the delivery of the infusion formulation is outside of a user basal range and, upon determining that the amount is outside of the user basal range, to receive the user-initiated event signal and initiate a variation in the delivery of the infusion formulation in accordance with the received user-initiated signal.

2. The infusion pump system recited in claim 1, wherein the variation in the delivery of the infusion formulation is substantially contemporaneous with the receipt of the user-initiated signal.

3. The infusion pump system recited in claim 1, wherein the sensing device for sensing the biological state comprises a sensing device for sensing a glucose level.

4. The infusion pump system recited in claim 1, wherein the computing element is programmed to regulate the delivery of an insulin formulation.

5. The infusion pump system recited in claim 4, wherein the computing element is programmed to initiate an event-based variation in the delivery of the insulin formulation which comprises at least one of an increase in an amount of the delivered insulin formulation and a decrease in an amount of the delivered insulin formulation.

6. The infusion pump system recited in claim 4, wherein the computing element is further programmed to initiate an event-based variation in the delivery of the insulin formulation which comprises a bolus delivery of the insulin formulation.

7. The infusion pump system recited in claim 1, wherein the user-initiated event signal is representative of at least one of a meal event, an exercise event, a stress event, a sleep event, and a medication event.

8. The infusion pump system recited in claim 7, wherein the communication device further communicates a user-initiated event ranking signal representative of an event ranking.

9. The infusion pump system recited in claim 8, wherein the computing element is further programmed to dynamically adjust the amount of infusion formulation delivered based on a first user-initiated event ranking signal when a second user-initiated event ranking signal is received by the computing element.

10. The infusion pump system recited in claim 1, wherein the communication device comprises a plurality of user-selectable operators corresponding to respective ones of a plurality of events, the user-selectable operators being selectable for communicating to the computing element the user-initiated signal.

11. The infusion pump system recited in claim 1, wherein the communication device comprises a plurality of user-selectable operators corresponding to respective ones of a plurality of event rankings.

12. The infusion pump system recited in claim 1, wherein the communication device comprises a display for displaying events and event rankings affecting the sensed biological state.

13. The infusion pump system recited in claim 12, wherein the communication device further comprises a plurality of user-selectable operators for selecting particular events and event rankings on the display and for initiating communication of the signals to the computing element, the signals representing the events and the event rankings.

14. The infusion pump system recited in claim 1, wherein the computing element is further programmed to maintain a history of user-initiated event signals.

15. The infusion pump system recited in claim 14, wherein the history is accessible to at least one of the user and the user's physician.

16. The infusion pump system recited in claim 1, wherein the pump is an implantable pump.

17. The infusion pump system recited in claim 1, wherein the computing element is programmed to compare the amount to at least one of a pre-programmed minimum value and a pre-programmed maximum value to determine whether the amount is outside of the user basal range.

18. An infusion pump system for use in delivery of an infusion formulation, the system comprising:
    a pump for delivering measured doses of an infusion formulation;
    a sensing device for sensing a biological state;
    a computing element communicating with the sensing device, the computing element being programmed to receive information about the sensed biological state from the sensing device and to regulate the delivery of the infusion formulation in accordance with the received information; and
    a communication device communicating with the computing element, the communication device for communicating a user-initiated event signal to the computing element, the user-initiated event signal being representative of an event affecting the sensed biological state;
    wherein the computing element is further programmed to receive the user-initiated event signal and initiate a variation in the delivery of the infusion formulation in accordance with the received user-initiated signal, and wherein the computing element is further programmed to perform diagnostics in order to verify that the user initiated event signal is consistent with a detected change in the sensed biological state.

19. The infusion pump system recited in claim 18, wherein the user is alerted when the user initiated event signal is not consistent with the detected change in the sensed biological state.

20. The infusion pump system recited in claim 18, wherein the closed-loop algorithm ceases an automatic control of the infusion pump and returns to a manual operation of the infusion pump when the user initiated event signal is not consistent with the detected change in the sensed biological state.

* * * * *